United States Patent
Cyphert et al.

(10) Patent No.: US 10,561,175 B2
(45) Date of Patent: Feb. 18, 2020

(54) ELECTRONIC VAPORIZER WITH LASER HEAT SOURCE

(71) Applicant: Healthier Choices Management Corp, Hollywood, FL (US)

(72) Inventors: Gilbert Cyphert, Phoenix, AZ (US); Edwin Balder, Mesa, AZ (US); Daniel Julia, Phoenix, AZ (US)

(73) Assignee: Healthier Choices Management Corp., Hollywood, FL (US)

( * ) Notice: Subject to any disclaimer, the term of this patent is extended or adjusted under 35 U.S.C. 154(b) by 368 days.

(21) Appl. No.: 15/683,719

(22) Filed: Aug. 22, 2017

(65) Prior Publication Data

US 2019/0059444 A1    Feb. 28, 2019

(51) Int. Cl.
| | | |
|---|---|---|
| *A61L 9/03* | (2006.01) | |
| *F24F 6/00* | (2006.01) | |
| *A24F 47/00* | (2006.01) | |
| *H01S 5/024* | (2006.01) | |
| *A61M 11/04* | (2006.01) | |
| *A61M 15/06* | (2006.01) | |
| *A61M 15/00* | (2006.01) | |

(52) U.S. Cl.
CPC ......... *A24F 47/008* (2013.01); *A61M 11/042* (2014.02); *A61M 15/0021* (2014.02); *A61M 15/06* (2013.01); *H01S 5/02453* (2013.01); *A61M 2205/368* (2013.01)

(58) Field of Classification Search
CPC .............. A24F 47/008; A61M 11/042; A61M 15/0021; A61M 15/06; A61M 2205/368; H01S 5/02453

USPC ................... 392/386–406; 219/121.6–121.83
See application file for complete search history.

(56) References Cited

U.S. PATENT DOCUMENTS

| | | | | |
|---|---|---|---|---|
| 4,402,574 A | * | 9/1983 | McConnel | B23K 26/1435 219/121.75 |
| 5,094,025 A | * | 3/1992 | Daniels | A01M 31/008 239/136 |
| 5,644,866 A | * | 7/1997 | Katsuda | A01M 1/2077 43/129 |
| 2017/0214261 A1 | * | 7/2017 | Gratton | H01M 10/446 |
| 2018/0289909 A1 | * | 10/2018 | Lindars | A61M 15/06 |

* cited by examiner

*Primary Examiner* — Sang Y Paik
(74) *Attorney, Agent, or Firm* — Berger Singerman, LLP; Geoffrey Lottenberg

(57) ABSTRACT

A vaporizer has a housing containing a power source. A laser assembly containing a laser module, such as a laser diode, is electrically coupled to the power source. A laser intensifier thermal transfer module contains a heating plate and is attached to the laser assembly. A cartridge assembly includes an inhalant supply cartridge containing inhalant, such as liquid or concentrate. The inhalant is in contact with the heating plate by way of a wick that draws the inhalant out of the supply cartridge. The laser assembly is receives electric current from the power source to activate the laser module causing the laser module to emit a beam directed toward the heating plate. The heating plate focuses the beam and generates heat sufficient to vaporize the inhalant. The inhalant is drawn through an air passageway in the cartridge for inhalation by the user.

17 Claims, 5 Drawing Sheets

ELECTRONIC VAPORIZER WITH LASER HEAT SOURCE

FIELD OF THE INVENTION

The present invention relates to electronic cigarettes and vaporizers.

BACKGROUND OF THE INVENTION

In any attempt to solve the problems of traditional smoking, electronic cigarettes and vaporizers have come to the forefront. These devices employ the use of a liquid or concentrate inhalants that often comprise a glycol ad-mixture of nicotine or other medicinal substances. The inhalant is drawn to and over a metal heating element, such as a metal coil, which coil receives electrical energy from an on-board battery. The electrical energy is converted to heat, thereby heating and vaporizing the inhalant brought in contact with the heating element. The vapor is then inhaled by way of a mouthpiece in fluid communication with an air channel disposed through the device.

The downside of traditional electronic cigarettes and vaporizer systems is that repeated heating and cooling of the metal heating element will cause transfer of heavy metals into the vaporizers liquid medium, resulting in inhalation of harmful and unwanted heavy metal material. Recent studies have in fact shown that heavy metal exposure caused by traditional electronic cigarettes and vaporizers is as harmful as or possibly more harmful than exposure to the carcinogens found in traditional cigarettes.

The nature of heating any material to the point of vaporization in a nontoxic manner where the element or compound phase transition from the liquid phase to vapor occurs in an inhalation device demands that safety protocols are generously incorporated. The present invention employs a laser heating system that is a radical departure from the common metal laser heat source (coil) based systems common of electronic cigarettes and vaporizers. The present invention demonstrates a key advantage in reduction of trace harmful elements such as heavy metals that have been shown to be delivered to the user due to direct contact of the liquid smoking medium to the traditional metal laser heat source.

Accordingly, the present invention is directed at reducing and/or eliminating heavy metal contamination found in traditional vaporizer systems. The nature of this laser vaping system is to eliminate this contamination possibility therefore making the engagement of "vaping" over long periods of time less susceptible to contamination to the human body.

It will be recognized that some or all of the Figures are schematic representations for purposes of illustration and do not necessarily depict the actual relative sizes or locations of the elements shown. The Figures are provided for the purpose of illustrating one or more embodiments of the invention with the explicit understanding that they will not be used to limit the scope or the meaning of the claims.

DETAILED DESCRIPTION

In the following description, for the purposes of explanation, numerous specific details are set forth in order to provide a thorough understanding of the vaporizer of the present invention. It will be apparent, however, to one skilled in the art that the vaporizer may be practiced without some of these specific details. Throughout this description, the embodiments and examples shown should be considered as exemplars, rather than as limitations on the vaporizer. That is, the following description provides examples, and the accompanying drawings show various examples for the purposes of illustration. However, these examples should not be construed in a limiting sense as they are merely intended to provide examples of the vaporizer rather than to provide an exhaustive list of all possible implementations of the vaporizer.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "some embodiments" or "one embodiment" or "an embodiment" means that a particular feature, structure or characteristic described in connection with the embodiment is included in at least one embodiment of the present invention. Thus, appearances of the phrases "in some embodiments" or "in an embodiment" in various places throughout this specification are not necessarily all referring to the same embodiment. Furthermore, the particular features, structures or characteristics may be combined in any suitable manner in one or more embodiments.

The present invention comprises various embodiments of a vaporizer system having a laser heat source. For purposes of this disclosure, the invention referred to as a "vaporizer" shall generally mean a personal inhalation device regarding of physical size or shape that is adapted for heating a target inhalation material such as liquid or medicinal concentrates. It is appreciated that is some embodiments the vaporizer herein may be considered or referred to as an "electronic cigarette" the purpose of same being to provide a smoking device as a supplement, replacement, or substitute for traditional smoking implements such as cigarettes.

Figure 1:
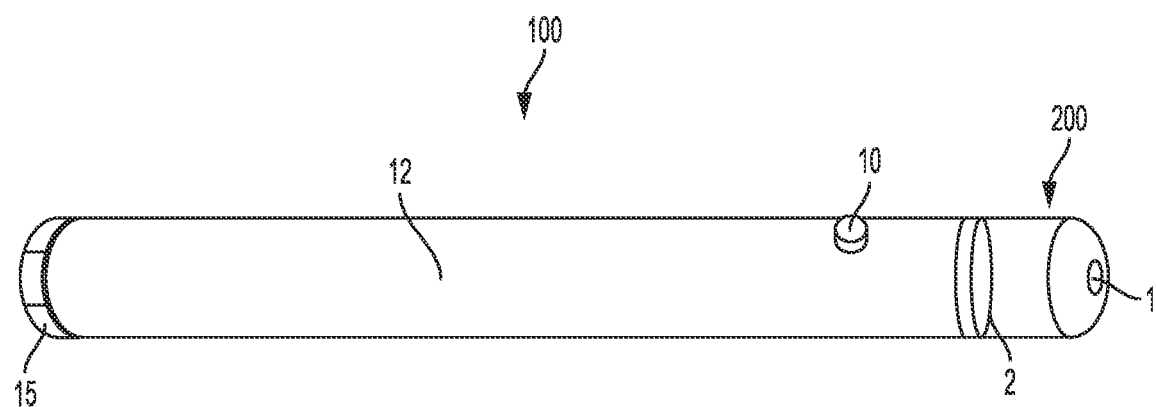
FIG. 1 is a perspective view of the vaporizer.

FIG. 1 a schematic of the vaporizer 100 comprising a substantially cylindrical housing 12 with a power connector end cap 15 at the distal end and a laser outlet 1 and its proximal end. An activation button 10 is located along the housing 12 at a predetermined location. Also shown is a focus adjustment knob 2 rotatably mounted and concentric with respect to the housing 12.

Figure 2:
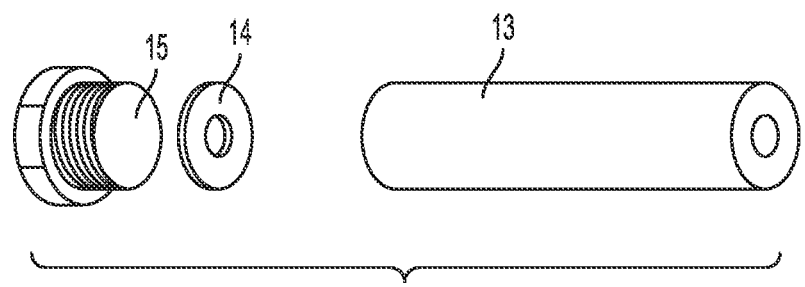
FIG. 2 is a exploded of one aspect of the vaporizer

With reference to FIG. 2, vaporizer 100 includes a power source 13 disposed within the housing 12, which power source is configured as a lithium-ion battery or other like energy storage device. An in-line annular insulator 14 is disposed distal of the power source 13 and disposed between the end cap 15 and the power source 13. The end cap 15 comprises an electric connector such as a USB-type connector or other similar power connection configured to recharge the power source 13. In some embodiments, a spring is provided in the end cap 15 to hold the power source 13 in place and to electrically couple the power source 13 to the laser driver circuit 5, shown in FIG. 3D. The end cap 15, in some embodiments, is configured to threadably engage the distal end of the power source 13. In other embodiments it may be permanently affixed so that the electrical components of the vaporizer 100 cannot be readily disassembled.

Figure 3A:
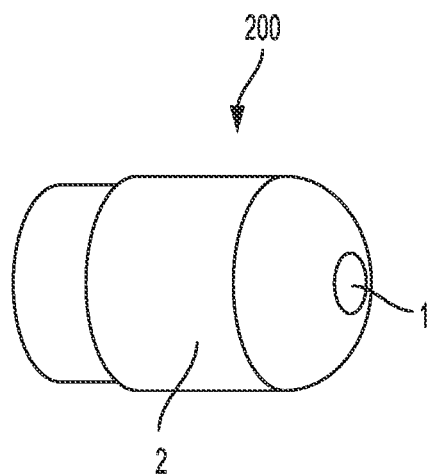
FIG. 3A is a close-up view of the laser heat source aspect of the vaporizer.
Figure 3B:
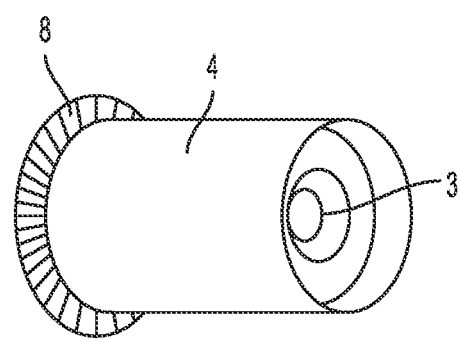
FIG. 3B is an exploded close-up view of the laser heat source aspect of the vaporizer.
Figure 3C:
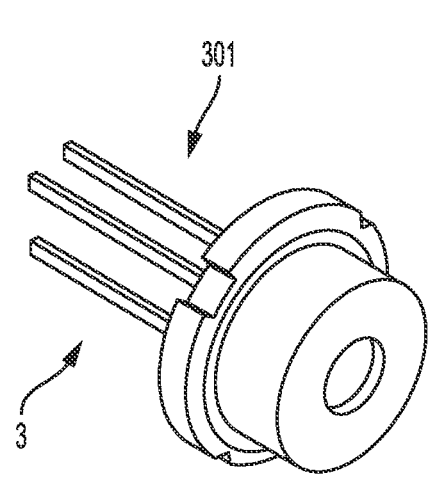
FIG. 3C is another close-up view of the laser heat source aspect of the e vaporizer.

With reference to FIG. 3A shown is a perspective view of the laser assembly 200, which comprises a laser output aperture 1 and a laser focus adjustment knob 2, distal from the aperture 1. The laser module 3 is shown in FIG. 3B encased by a laser contaminate shield casing 4. A heat sink 8 is provided distal of the laser module 3 at the end of the casing 4. The laser module 3 is disposed within the laser assembly 200 at the proximal end of the vaporizer 100. The laser module 3 is shown in isolation in FIG. 3C and comprises one or more prongs 301 to provide electrical connection to the laser driver circuit 5 and in turn the power source 13, as further described herein.

Figure 3D:
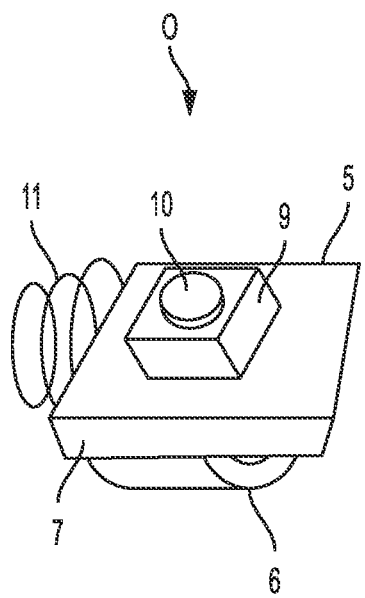
FIG. 3D is a section view of the laser driver circuit.

FIG. 3D shows the laser driver circuit 5 in section view. The driver circuit 5 is disposed within the housing 12 either at the distal end adjacent to the end cap 15, or toward the proximal end adjacent to but distal of the laser assembly 200. The driver circuit 5 comprises a locating frame 6 with an insulating plate 7 mounted thereon. A limited duration power switch circuit 9 is mounted to the insulating plate 7 and is activated by button 10, which button 10 extends outwardly of the housing 12 to be accessed externally. A power supply connection spring 11 electrically couples the power source 13 to the components of the laser driver circuit 5, which components are in turn electrically coupled to the laser module 3. In some embodiments the laser driver circuit 5 is disposed between the proximal end of the power source 13 and the laser assembly 200. The button 10 is configured to switch the driver circuit 5 on and off in order to draw power from the power supply 13 to the laser module 3.

Figure 4:
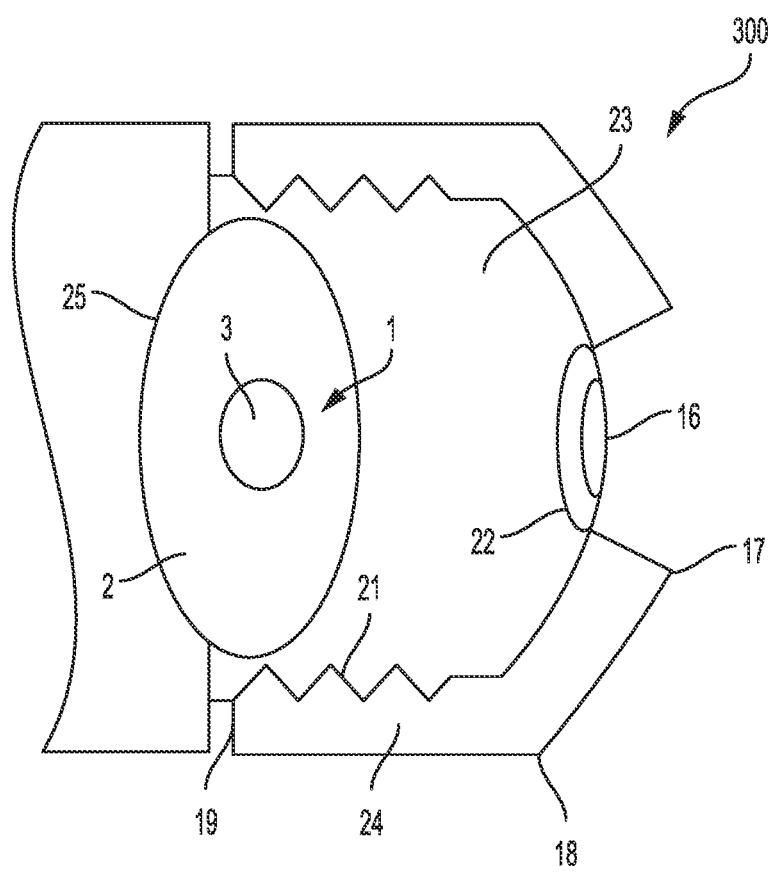
FIG. 4 is section view of the laser heat source aspect of the vaporizer.

FIG. 4 is a close-up section view of vaporizer 100 showing additional components. A laser intensifier thermal transfer module (LITTM) 300 is attached to the laser assembly 200, wherein upon activation of the laser module 3 by the button 10, which transfers electrical energy from the power source 13 to the module 3, the resultant laser beam is manipulated. The LITTM 300 includes an internal chamber 23 housed inside an insulating outer wall 18. In some embodiments, insulation 24 is disposed between the outer wall 18 and the chamber 23. A thermal vent 19 is disposed between the distal end of the LITTM 300 and the laser assembly 200 to allow excess heat to escape as necessary.

Figure 6:
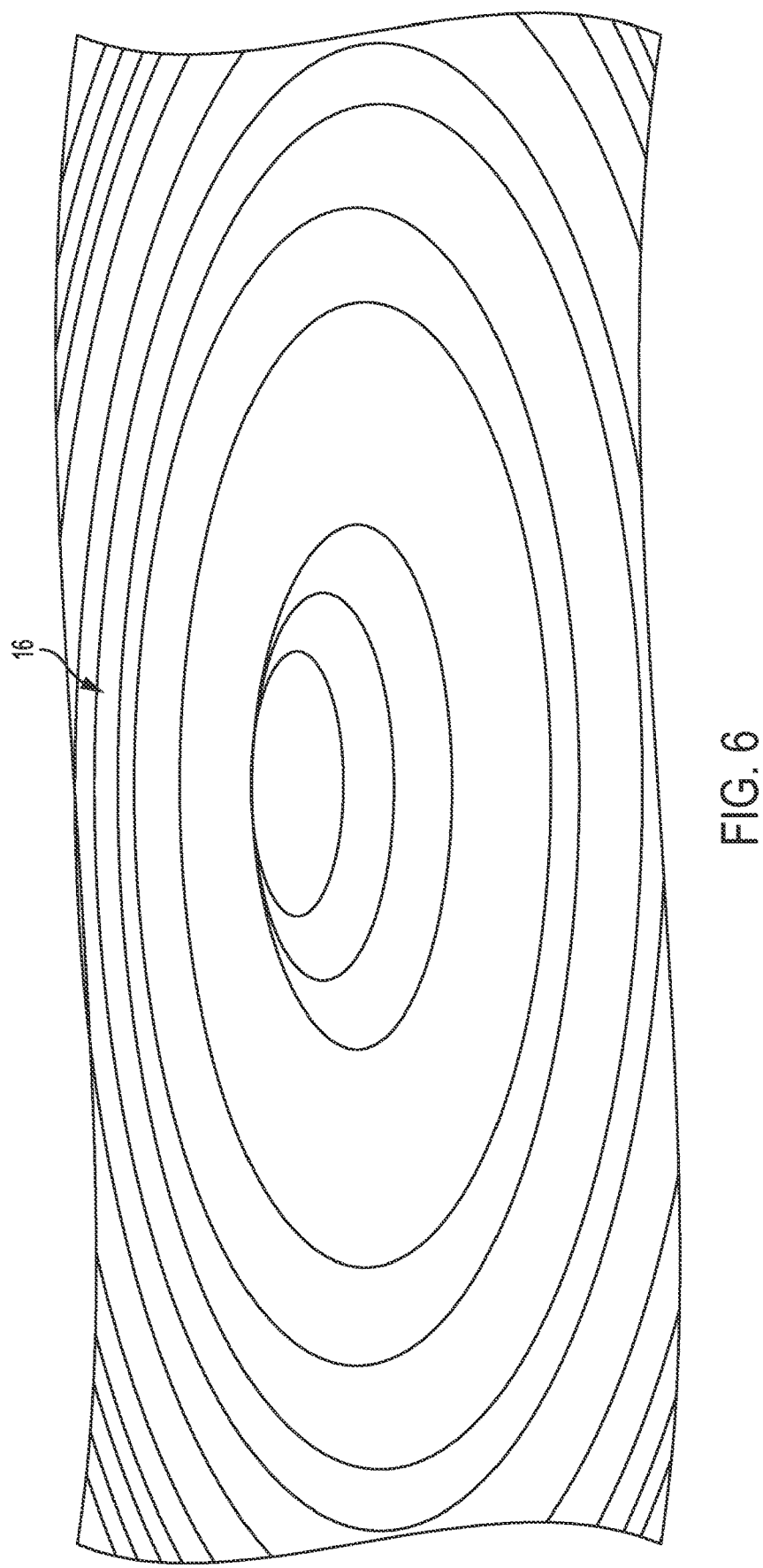
FIG. 6 is an example of the configuration of the heating plate of the vaporizer.

Upon activation, the laser beam exiting the laser module 3 is focused to hit the thermal energy surface plate 16, which in some embodiments has a mushroom or disk-shaped configuration as shown in FIG. 6. The plate 16 is encased by an intensifier absorption deflection ring 22 which aids in absorbing excess heat while transferring reflected beams to a number of targeted angled reflective laser intensifiers 21 disposed in the chamber 23 of the LITTM 300. The electrical junction 25 of the power source 13 and the laser module 3 is designed such that the laser module 3 can be removed and replaced as desired. The distal end of the LITTM 300 includes a cartridge receptacle 17 adjacent to the heating plate 16 on which the cartridge 27 seats as further described herein.

When a laser beam exits the laser module 3 it is beamed into the LITTM 300 chamber 23 and focused to hit the heating plate 16 while any reflective beams caused by an inaccurate aim are reflected off the deflection ring 22. In some embodiments, the deflection ring 22 is coated with nontoxic titanium nitride or similar safe reflective surface. In some embodiments, this same material is coated throughout the internal surface of the chamber 23 so that any unfocused beams are reflected and targeted back to the heating plate 16 off of the targeted angled reflective laser intensifiers 21, thereby intensifying the laser beam and thus the magnitude of thermal transfer to the heating plate 16.

This system featuring beam capture and refocus to the intended target, i.e. heating plate 16, allows for the most effective and efficient thermal transfer possible under a variety of operating conditions and types of lasers employed. The LITTM 300 feature allows the unit to more efficiently reach vaporization temperatures at far less power achieving results only seen in higher power lasers. The LITTM 300 will reduce the expense incurred in manufacturing extreme and precise targeting systems of lasers to always obtain the desired results.

Figure 5:
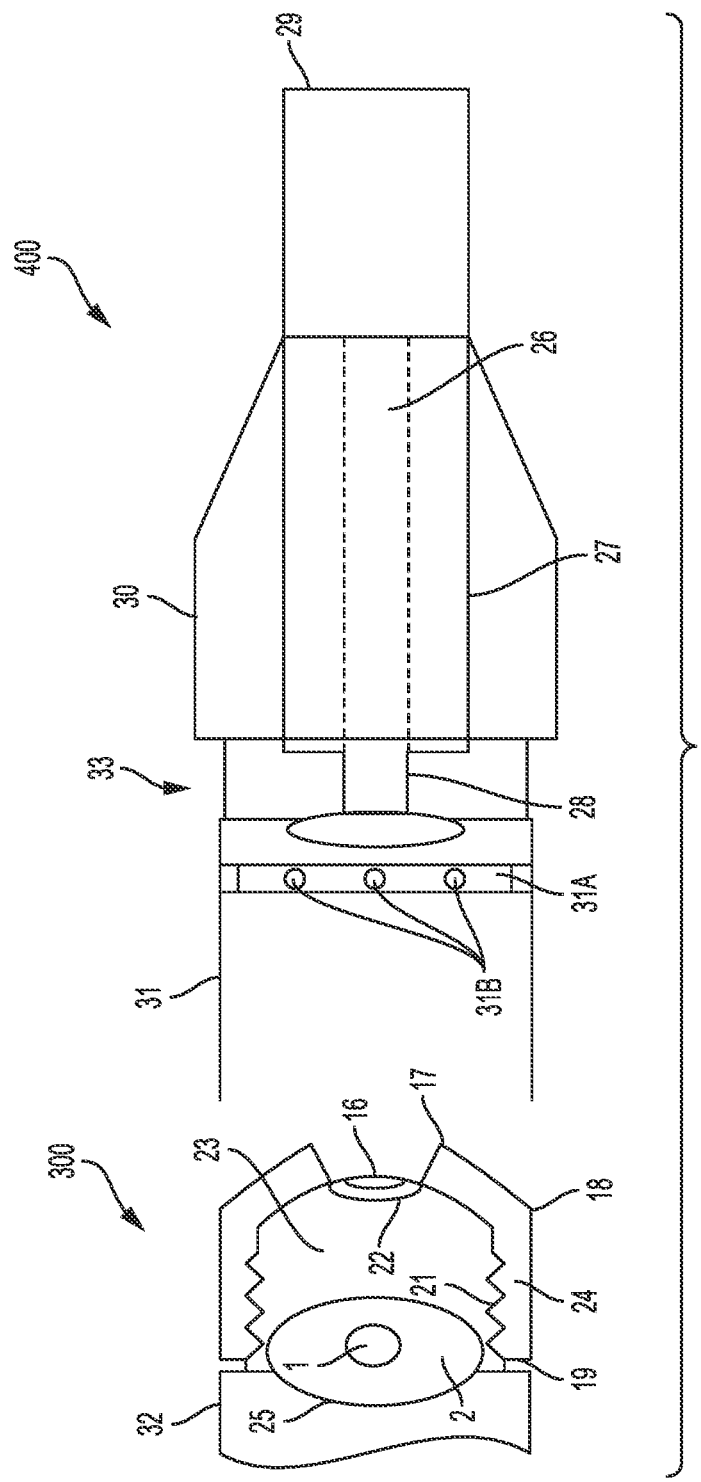
FIG. 5 is section view of the proximal end of electronic cigarette or vaporizer.

With reference to FIG. 5, the LITTM 300 includes a connecting adapter 32 that is configured to receive a cartridge assembly 400. The cartridge assembly 400 houses an inhalant or liquid supply cartridge 27 to which heat from the laser is applied for vaporization. The cartridge assembly 400 includes a sleeve 31 that is received over the connecting adapter 32. The sleeve 31 includes a fluid inlet housing 31A that comprises a plurality of selectively openable inlet orifices 31B. In some embodiments, a manually slideable cover is disposed over the inlet orifices to allow the user to vary the volume of airflow into the system. The inlet orifices, therefore, are configured to draw fluid external to the device into the cartridge 27 as further described.

A cartridge housing 30 extends from the sleeve 31 and contains the supply cartridge 27. The cartridge assembly 400 is axially aligned to the LITTM 300 such that that the cartridge 27 is centered with respect to the cartridge receptacle 17 and snugly adjacent to the thermal transfer plate 16. Cartridge 27 comprises a distal wick 28 that comes in direct physical contact with the heating plate 16. The cartridge 27 further includes an internal air channel 26 that is devoid of the inhalant medium that is otherwise contained in the cartridge 27. The air channel 26 is in fluid communication with the inlet orifices 31B of the sleeve 31 such that applying suction at the mouthpiece 29 will create a vacuum that draws air through the orifices 31B, into the channel 26 and out of the mouthpiece 29 while gathering heated vaporized inhalant from the cartridge 27.

When the vaporizer 100 is activated, electrical energy from the power source 13 turns on the laser module 3 which causes the heating plate 16 to heat up. Heat from the plate 16 vaporizers the liquid inhalant medium within cartridge 27 by way of wick 28, which wick 28 draws liquid from the body of the cartridge 27 to surface of the heating plate 16. The liquid then vaporizers and can be drawn through the mouthpiece 29 by applying suction by mouth or other means which draws air external to the device into inlet orifices 31B, through the air channel 26 of the cartridge 27, and to and through the mouthpiece 29. As shown, the mouthpiece 29 extends proximally from the cartridge housing and, in some embodiments, tapers to form a comfortable nozzle for the user to inhale from.

The sleeve 31 insulates and protects against the transmission of heat from the heating plate 16 and other system components. The sleeve 31 also functions as an alignment guide and in conjunction with the mouthpiece 29 and acts as a way for the wick to be properly positioned and translated down to the heating plate 16. In some embodiments, the sleeve 31 also includes an opening 33 to allow for medical concentrates to be placed directly onto the heating plate 16 for vaporization through the mouthpiece when the cartridge 27 is removed and replaced with a concentrate pass-through safety filter. In some embodiments, a small indentation is provided on the heating plate 16 at the location of the receptacle 17 in order to retain concentrates or other material for vaporization.

In some embodiments, the power switch circuit 9 of the laser driver circuit 5 comprises a microprocessor containing control logic which includes activation and locking capability. When the pressable button 10 is pressed a predetermined number of times within a predetermined time period, the power source 13 is locked (i.e., power is unavailable to any component of the vaporizer 100). When the pressable button (not shown) is a predetermined number of times within a predetermined time period, again, the power source 13 is unlocked. This safety feature ensures that the vaporizer 100 will not begin heating the heating plate 16 when the vaporizer is located in a user's pocket or other when not in use. In some embodiments, power switch circuit 9 may comprise an embedded data processor connected via an internal bus to a read only memory containing the executable code for causing the microprocessor to perform the functions described herein. In another embodiment, the power switch circuit 9, or chip may comprise one or more electronic circuits that employ one or more switches to perform the functions described herein.

In some embodiments, the laser module 3 of the vaporizer 100 comprises a vertical cavity surface emitting laser diode (VCSEL). In other embodiments, the laser module 3 comprises an edge emitting laser diode. VCSEL diodes have the unique feature of emitting their beam from either their top or bottom surface. Unlike edge emitting laser diode which is 250 to 500 um in length, the full dimension of a VCSEL is limited only by the dimensions of the emitting region needed for electrical contacts. The result is a functioning VCSEL can designed to be only a bit larger than the beam dimension making the laser vaporizers 100 significantly more compact and user friendly then current non-laser vaporizer units.

It is to be noticed that the term "comprising," used in the claims, should not be interpreted as being limitative to the means listed thereafter. Thus, the scope of the expression "a device comprising means A and B" should not be limited to devices consisting only of components A and B. It means that with respect to the present invention, the only relevant components of the device are A and B. Put differently, the terms "including", "comprising" and variations thereof mean "including but not limited to", unless expressly specified otherwise. Similarly, it is to be noticed that the term "coupled", also used in the claims, should not be interpreted as being limitative to direct connections only. Thus, the scope of the expression "a device A coupled to a device B" should not be limited to devices or systems wherein an output of device A is directly connected to an input of device B. It means that there exists a path between an output of A and an input of B which may be a path including other devices or means. The enumerated listing of items does not imply that any or all of the items are mutually exclusive, unless expressly specified otherwise. The terms "a", "an" and "the" mean "one or more", unless expressly specified otherwise. Elements of the invention that are in communication with each other need not be in continuous communication with each other, unless expressly specified otherwise. In addition, elements of the invention that are in communication with each other may communicate directly or indirectly through one or more other elements or other intermediaries.

Thus, it is seen that a laser powered vaporizer is provided. One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims. The fact that a product, process or method exhibits differences from one or more of the above-described exemplary embodiments does not mean that the product or process is outside the scope (literal scope and/or other legally-recognized scope) of the following claims.

The invention claimed is:
1. A vaporizer, comprising:
a housing containing a power source;
a laser assembly containing a laser module wherein the laser module is electrically coupled to the power source;
laser intensifier thermal transfer module containing a heating plate and a laser deflection ring surrounding the heating plate, wherein the laser intensifier thermal transfer module is attached to the laser assembly;
and a cartridge assembly comprising an inhalant supply cartridge containing inhalant, wherein the inhalant is in contact with the heating plate; and
wherein the laser assembly is structured to receive electric current from the power source to activate the laser module, which laser module emits a beam directed toward the heating plate, the heating plate configured to generate heat to vaporize the inhalant.

2. The vaporizer of claim 1, wherein the housing includes an end cap having an electrical connector to charge the power source.

3. The vaporizer of claim 1, wherein the laser assembly includes a heat sink and a casing surrounding the laser module.

4. The vaporizer of claim 1, wherein the laser module comprises a vertical cavity surface emitting laser diode.

5. The vaporizer of claim 1, wherein the laser intensifier thermal transfer module comprises an insulated cavity having one or more angled reflective laser intensifiers to reflect and focus the beam toward the heating plate.

6. The vaporizer of claim 1, wherein the cartridge assembly includes a sleeve received over the laser intensifier thermal transfer module.

7. The vaporizer of claim 1, wherein the cartridge assembly includes a mouthpiece proximal of the inhalant supply cartridge.

8. The vaporizer of claim 7, wherein the inhalant supply cartridge includes an air channel configured to pass vaporized inhalant from the heating plate through the mouthpiece.

9. The vaporizer of claim 1, wherein the inhalant supply cartridge includes a wick in contact with the heating plate, the wick configured to drawn inhalant from the cartridge to the heating plate.

10. A method of vaporization using a vaporizer, comprising:
applying electrical current to a laser module such that the laser module emits a beam;
focusing the beam from the laser module against a heating plate proximal from the laser module;
generating heat at the heating plate as a result of the focusing step;
drawing inhalant to the heating plate from an inhalant supply cartridge;
vaporizing the inhalant as a result of application of the heat to the inhalant;
drawing the vaporized inhalant out of the inhalant supply cartridge;
wherein the vaporizer comprises:
a housing containing a power source;
a laser assembly containing a laser module wherein the laser module is electrically coupled to the power source;
laser intensifier thermal transfer module containing a heating plate and a laser deflection ring surrounding the heating plate, wherein the laser intensifier thermal transfer module is attached to the laser assembly;
and a cartridge assembly comprising an inhalant supply cartridge containing inhalant, wherein the inhalant is in contact with the heating plate; and
wherein the laser assembly is structured to receive electric current from the power source to activate the laser module, which laser module emits a beam directed toward the heating plate, the heating plate configured to generate heat to vaporize the inhalant.

11. The method of claim 10, wherein the housing includes an end cap having an electrical connector to charge the power source.

12. The method of claim 10, wherein the laser assembly includes a heat sink and a casing surrounding the laser module.

13. The method of claim 10, wherein the laser module comprises a vertical cavity surface emitting laser diode.

14. The method of claim 10, wherein the laser intensifier thermal transfer module comprises an insulated cavity having one or more angled reflective laser intensifiers to reflect and focus the beam toward the heating plate.

15. The method of claim 10, wherein the cartridge assembly includes a sleeve received over the laser intensifier thermal transfer module.

16. The method of claim 10, wherein the cartridge assembly includes a mouthpiece proximal of the inhalant supply cartridge.

17. The method of claim 10, wherein the inhalant supply cartridge includes a wick in contact with the heating plate, the wick configured to drawn inhalant from the cartridge to the heating plate.

* * * * *